United States Patent [19]
Van Der Zel

[11] Patent Number: 5,378,154
[45] Date of Patent: Jan. 3, 1995

[54] DENTAL PROSTHESIS AND METHOD FOR MANUFACTURING A DENTAL PROSTHESIS

[75] Inventor: Joseph M. Van Der Zel, Zwaag, Netherlands

[73] Assignee: Elephant Holding B.V., Netherlands

[21] Appl. No.: 40,896

[22] Filed: Mar. 31, 1993

[30] Foreign Application Priority Data

Apr. 6, 1992 [NL] Netherlands ............... 92.00643
Apr. 6, 1992 [NL] Netherlands ............... 92.00644

[51] Int. Cl.⁶ ............................. A61C 5/10; A61C 5/08
[52] U.S. Cl. .................................... 433/223; 433/218
[58] Field of Search ............... 433/214, 215, 218, 219, 433/223, 229, 202.1

[56] References Cited

U.S. PATENT DOCUMENTS

| | | | |
|---|---|---|---|
| 4,411,626 | 10/1983 | Becker et al. | 433/223 |
| 4,478,580 | 10/1984 | Barrut | 433/223 |
| 4,575,805 | 3/1986 | Moermann et al. | 433/223 X |
| 4,663,720 | 5/1987 | Duret et al. | 433/214 X |
| 4,742,464 | 5/1988 | Duret et al. | 433/214 |
| 4,937,928 | 7/1990 | van der Zel | 433/223 X |
| 5,027,281 | 6/1991 | Rekow et al. | 364/474.24 |
| 5,092,022 | 3/1992 | Duret | 433/213 X |

*Primary Examiner*—Gene Mancene
*Assistant Examiner*—Nicholas D. Lucchesi
*Attorney, Agent, or Firm*—Curtis, Morris & Safford

[57] ABSTRACT

A method for manufacturing a dental prosthesis, such as a dental crown, wherein at least the visible part of the prosthesis (the outside) is subjected to a material removing operation by means of a numerically controlled micro machine tool and wherein the machining paths are visible on the final prosthesis. The machining paths follow a three-dimensionally curved line and do not lie in a flat plane. The dental prosthesis which is manufactured in this manner has a natural-looking appearance. According to another aspect of the invention the shape of the dental prosthesis is such that near the edge of the prosthesis the cement layer is thicker than at some distance from the edge to relieve the edge of the dental prosthesis from bearing heavy forces.

9 Claims, 2 Drawing Sheets

DENTAL PROSTHESIS AND METHOD FOR MANUFACTURING A DENTAL PROSTHESIS

FIELD OF THE INVENTION

The invention relates to a dental prosthesis, such as a dental crown, an inlay, a veneer (facet) or a bridge, and to a method for manufacturing such dental prosthesis.

BACKGROUND OF THE INVENTION

Such a method is known from U.S. Pat. No. 5,027,281, wherein a dental prosthesis is made from a massive block of material. Material is thereby removed from the block of material by means of a numerically controlled micro milling machine. After the shape of the prosthesis has been determined and stored in the memory of a computer, the computer calculates the machining paths which the miller is to follow. The machining paths are determined by means of flat, mutually parallel sections of the intended prosthesis. Consequently the machining path which the milling tool follows during the material removing operation lies in a flat plane at all times. In order to remove the machining paths which the final material removing operation leaves behind, the surface is polished, for example by means of a rotating brush.

U.S. Pat. No. 4,937,928 describes a method for manufacturing a dental prosthesis, wherein the prosthesis is formed on a model in the shape of the part of the teeth on which the prosthesis is to be provided. The prosthesis is thereby produced by successively applying a number of layers of material on the model. After the application of each layer the workpiece is worked by means of a numerically controlled machine tool. The machining paths which the tool follows during this operation are computed by means of a CAD/CAM system.

A drawback of the known method is that either the machining paths must be spaced so closely that the individual paths on the final product are no longer visible, which is very laborious, or the workpiece must be subjected to an intensive polishing or grinding operation, in order to obtain an aesthetically sound result. Such a polishing operation is usually carried out by hand.

The material which is used for a dental prosthesis must satisfy a number of varying requirements. Besides requirements relating to the color and machinability, the material must be sufficiently hard, which generally entails a certain degree of brittleness. This is particularly so when use is made of materials such as porcelain or glass especially suitable for mechanical dentistry because of their machinability. In order to obtain sufficient strength, in spite of brittleness, it is not unusual to provide the inner side the dental prosthesis, which is not visible once the prosthesis is fitted, with a metal layer. This metal layer may even comprise a thickness of a few tenths of a millimeter and extend across the entire inner surface of the prosthesis.

The dental prosthesis is fitted on the dental element in question with the interposition of a cement layer. The cement layer generally comprises a thickness of up to about 0.3 mm and is sufficiently strong for transmitting the forces which are exerted on the prosthesis to the dental element in question, especially during chewing.

When the dental prosthesis substantially consists of a relatively brittle material, the most vulnerable place for a fracture to occur is in the area near the edge of the prosthesis, i.e. in the area where the prosthesis joins the teeth. Since the part of the teeth in question is prepared —in advance—up to the place where the edge of the prosthesis joins the teeth. Where the edge of the prosthesis joins the teeth is called the preparation line, which, in case of a dental crown, generally extends around the dental element in question, near the part of the jaw where the dental element is implanted. The edge of the prosthesis therefore corresponds with the preparation line of the dental element in question.

In order to obtain a good connection of the prosthesis to the part of the teeth in question at the location of the preparation line, the prosthesis comprises a relatively thin part near the edge. When a reinforcement in the form of a metal layer is used, a metal layer is provided especially in that area, in order to strengthen this area.

OBJECTS OF THE INVENTION

A first object of the invention is to provide a method for manufacturing a dental prosthesis, wherein an aesthetically sound dental prosthesis is obtained in an effective manner by carrying out a material removing operation by means of a micro machine tool.

A second object of the invention is to provide a dental prosthesis being shaped such that forces exerted on the prosthesis hardly place a load, if at all, on the edge area of the prosthesis.

SUMMARY OF THE INVENTION

In order to accomplish the first objective of the invention the prosthesis is worked in such a manner, that the machining path follows a three-dimensionally curved line, i.e. deviates from a path in a flat plane.

In practice it has become apparent that when a dental prosthesis is subjected to a material removing operation, deviations from machining paths lying in a flat plane will; create a natural-looking result, which is aesthetically even better-looking than a dental prosthesis with a polished surface. This contrasts sharply with the appearance of a dental prosthesis comprising machining paths in a flat plane, which appearance is unacceptable.

According to one aspect of the invention the three-dimensionally curved machining paths may follow the natural lines of the surface of the teeth. This makes it possible so that, for example, a groove (fissure) is produced in the tooth surface by having the tool follow the path of the groove during the material removing operation.

According to another aspect of the invention the outer side of a prosthesis, which is formed in the shape of a tooth, is worked by following substantially circular machining paths around the tooth, whereby the mutual distance of the machining paths varies locally. At local protrusions in the tooth surface, where the radius of the substantially circular machining path is relatively smaller, the mutual distance of the machining paths is slightly increased, which gives the prosthesis a natural-looking appearance.

The outer surface of a dental prosthesis can be determined by taking a so-called library model as a starting point, i.e. making a selection from a number of typical models of teeth whose shape is laid down, for example in the memory of a computer. After a selection has been made with regard to the model which will serve as a starting point, the model in question will have to be adapted to the specific circumstances and the space which is available for the prosthesis. This may be done by hand by displaying the prosthesis in the shape of the library model on a computer screen. The computer then calculates and points out, on the basis of data of the teeth in question and the relevant jaw movements, at what locations the prosthesis needs to be adapted. The adaptation may be effected by moving a pointer across the screen, by means of a mouse, and clicking the mouse at positions where problems occur, after which the computer calculates an adapted shape and displays it on the screen. These operations may be repeated until a shape of the prosthesis is obtained which satisfies all requirements. The machining paths associated with this shape, in order to manufacture the prosthesis by means of a material removing operation, may then be computed by the computer and be transferred to a numerically controlled machine tool.

It is also possible to take the shape of the corresponding part of the teeth in the other jaw half as a starting point for the shape of the prosthesis. This shape may be registered by means of a three-dimensional scanner and be mirrored and subsequently recorded in the memory of the computer. The scanning generally takes place by repeatedly determining in a flat plane the line of intersection with the surface of the teeth. The amount of data required for recording a surface scanned in such a manner can be considerably reduced by converting the data which into data records the intersection points of a network of lines. The number of these lines, and thus the amount of data, can be further reduced by having the lines follow the shape of the surface of the teeth, i.e. placing lines in particular in grooves that are present. This may take place by displaying the surface obtained by means of the scanner on a computer screen. Subsequently a pointer is clicked at characteristic locations in a groove by means of a mouse, after which the computer carries out a conversion computation, whereby the intersection points of lines are put at the indicated places. In practice it has become apparent that in this manner it is possible to record the shape of a dental crown with a limited number of intersection points, for example from 500–2000.

According to the invention a dental prosthesis may be formed in that during the material removing operation the lines are followed in of which the computer has recorded the shape of the prosthesis in the above-described manner.

The invention furthermore relates to a dental prosthesis, of which at least the outside (the visible side) has undergone a material removing operation by means of a numerically controlled machine tool, whereby according to the invention the machining paths of the material removing operation are visible and wherein the machining paths follow three-dimensionally curved lines. According to a further aspect of the invention machining paths follow grooves of the prosthesis.

In order to accomplish the second objective of the invention the shape of the inner surface of the dental prosthesis, according to the invention, is such that near the edge of the prosthesis, i.e. near the preparation line, a thicker cement layer is provided than at some distance from the edge, e.g. at the location where the prosthesis is thicker and thus stronger. At that location the thickness of the cement layer can even be reduced to such an extent that in fact there is direct contact between the prosthesis and the prepared part of the teeth.

The forces which are exerted on the prosthesis, for example during chewing, are transmitted to the dental element on which the prosthesis is fitted via the cement layer. Because the cement exhibits a certain elasticity, a somewhat even distribution of the forces takes place. By locally varying the thickness of the cement layer in a suitable manner, however, the location where the forces are transmitted may be influenced. When an area comprising a thicker cement layer bounds an area comprising a thinner cement layer, the thicker cement layer will behave more elastically and the thin cement layer will behave more rigidly, so that the forces to be transmitted will be substantially transmitted in the area where the cement layer is thinner.

According to the invention the prosthesis is formed in such a manner that the cement layer is thicker near the edge, so that the edge area of the prosthesis, where the prosthesis is relatively thin, is relieved from transmitting larger forces. The forces will primarily be transmitted in the area at some distance from the edge where, because of its shape, the prosthesis is stronger. For that purpose a thinner cement layer is present at that location, or the prosthesis is in direct contact with the prepared part of the teeth at that location.

According to the invention the thicker cement layer may extend across a 0.1–3 mm wide strip along the edge. According to a further aspect of the invention the area having a thinner cement layer and/or where there is direct contact between the prosthesis and the prepared part of the teeth, where the forces are primarily transmitted, may extend across an annular strip at some distance from the edge of the prosthesis, so that the area where larger forces are transmitted is thus confined to the thicker, and consequently stronger parts of the prosthesis.

When the dental prosthesis is provided with a metal layer at its inner side, according to a further aspect of the invention the metal layer may terminate at some distance from the edge of the prosthesis, so that it will not be visible. Since, as noted above, the edge area of the prosthesis is relieved from the larger forces, the reinforcement by means of the metal layer in that area may be eliminated. The fact that in this manner the metal layer is not visible constitutes a significant aesthetic advantage.

When the metal layer extends across the entire inner surface of the prosthesis, with the exception of the edge area as indicated above, the metal layer may, according to the invention, be thickened, and as a result reinforced, so as to form an annular strip along the edge of the metal layer. In this way, an extra reinforcement of the prosthesis is obtained in the area where the forces are primarily transmitted.

By using the invention the area where the forces are primarily transmitted can be restricted in such a manner that, according to another aspect of the invention, the reinforcing metal layer on the inner surface of the prosthesis is reduced to only an annular strip or band near, but spaced from the edge of the prosthesis.

The invention furthermore relates to a method for manufacturing a dental prosthesis as described above. Such a method is described in U.S. Pat. No. 4,937,928. According to that method first a model (replica) of the prepared dental element is made, with the model including additional material (allowance) for the cement layer that is to be inserted. The outer surface of the model therefore corresponds with the inner surface of the prosthesis to be manufactured. The preparation line forms the demarcation between the prepared part of the dental element, on which the prosthesis is fitted, and the part of the teeth which is not going to be covered by the prosthesis. The prosthesis will be formed on the model, up to the preparation line, after which the model is removed, for example by milling it off, so that the dental prosthesis remains.

According to one aspect of the invention the model is shaped such that near the preparation line the additional material for the cement layer is thicker than at some distance from the preparation line.

By locally varying the additional material in the model the thickness of the cement layer may, according to the invention, be adapted to the desired load distribution during use of the prosthesis.

In order to more fully explain the invention, embodiments of the invention will be described in more detail hereafter with reference to the drawing. Although a dental crown has been taken as an example, the invention similarly relates to other dental prostheses, such as an inlay, a facet or a bridge.

DETAILED DESCRIPTION OF A PREFERRED EMBODIMENT

The Figures are merely diagrammatic illustrations, showing proportions deviating from the actual proportions for the sake of clarity.

Figure 1:
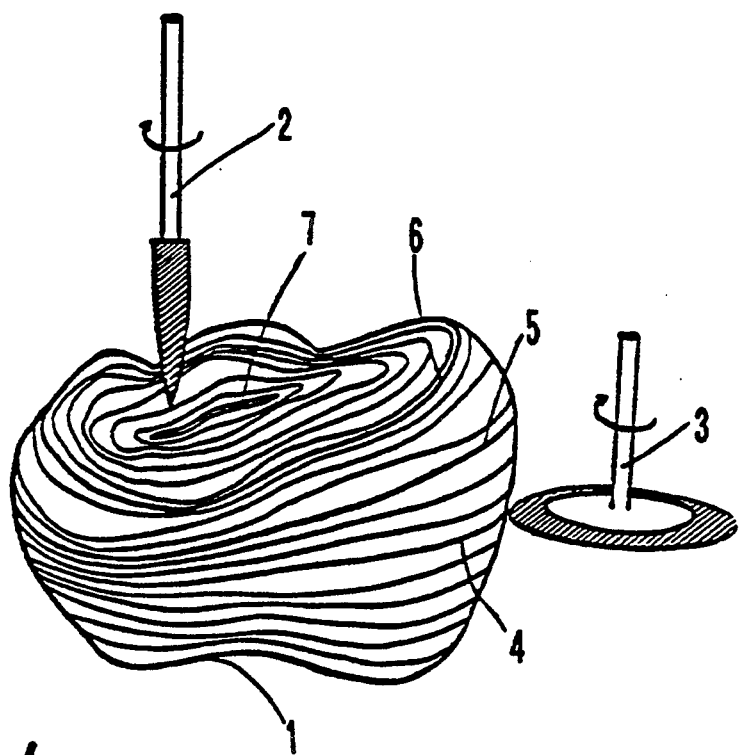
FIG. 1 shows a dental crown, on which machining paths are indicated.

FIG. 1 shows a dental crown, which is bounded by the preparation line 1 at the bottom side. The dental crown has undergone a material removing operation by means of, for example, a pointed burr 2 and a disc cutter 3. These tools are shown merely diagrammatically and not in proportion. The dental crown is shown to have machining paths 4, i.e. the paths along which the material removing operation has taken place. The machining paths 4 are shown diagrammatically and not in proportion for that matter. In practice the mutual distance of the machining paths will be, for example, 0.02–0.2 mm. A number of machining paths 4 follow a characteristic path about the crown, such as the equatorial line 5 (which constitutes the circumference of the crown in vertical projection), the so-called "cusp line" 6 (which runs over the highest parts of the crown) and the so-called "fossa" 7 (the deepest part of the upper side of the dental crown).

The above-mentioned characteristic lines, as well as other characteristic lines of the dental crown, may be established by displaying the dental crown, whose shape is recorded in the memory of a computer, on a screen. A pointer is moved across the screen by means of a mouse and the mouse is clicked when the pointer is located in characteristic positions. The characteristic positions and lines may also be established by means of calculations by the computer, since the lines and positions are determined by the shape of the dental crown stored in the computer.

As is apparent from FIG. 1, the machining paths extend in an irregular-looking pattern, which is shown out of proportion for that matter. As a result of this irregular pattern the dental prosthesis has a natural appearance when fitted in the patient's mouth.

Figure 2:
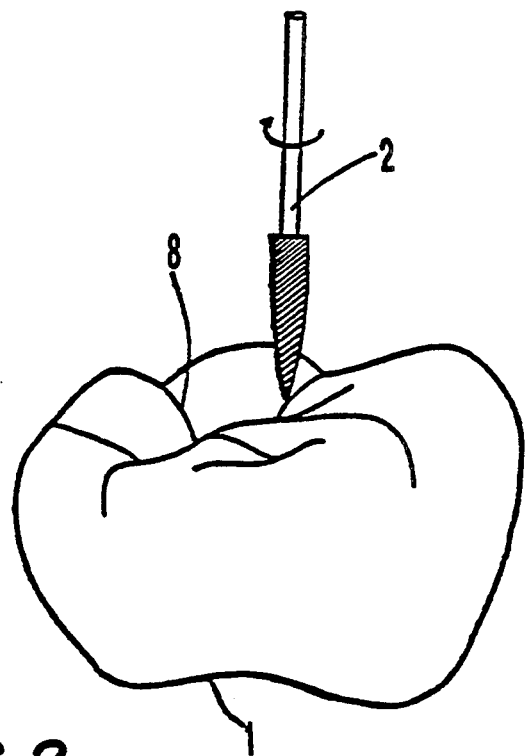
FIG. 2 shows a dental crown, which is undergoing a finishing operation.

FIG. 2 shows a dental crown in elevational view. The dental crown at its bottom side is bounded by the preparation line 1 and exhibits a number of primary and secondary fissures 8 at its upper side. The fissures 8 constitute characteristic lines at the upper side of the dental crown and may form the machining path for e.g. the pointed burr 2 during the material removing operation of the crown. This milling operation may form part of the operation explained with reference to FIG. 1. However, the milling may also be a finishing operation, which is carried out after the final form of the prosthesis has been substantially achieved.

Figure 3:
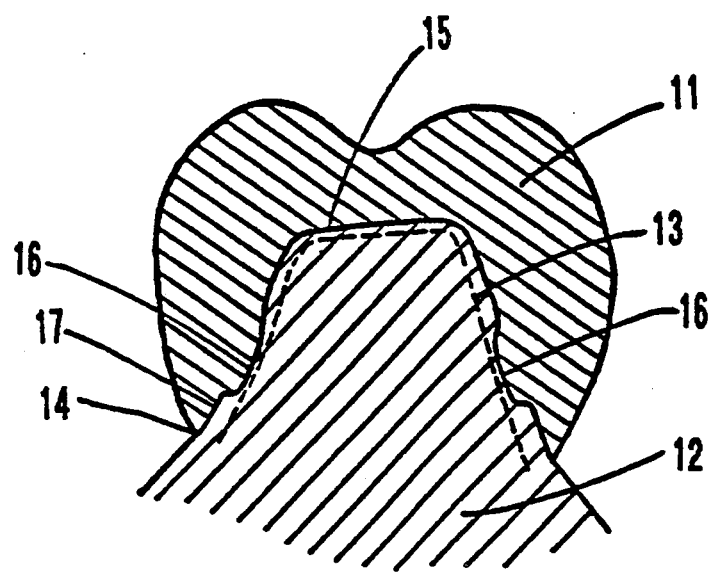
FIG. 3 shows a dental crown present on the model on which the dental crown has been formed.

FIG. 3 shows a dental crown 11 made on a model 12 illustrated in sectional view. The model is for example made of a fire-resisting material, such as fine-grained magnesium oxide, or another material which can be readily worked by means of a milling cutter. The model 12 may be made by scanning the relevant prepared part of the teeth by means of a three-dimensional scanner. The data thus obtained is supplied to a CAD/CAM system, which determines the shape of the crown on the basis of the data. In this way the shape of the model 12 is determined. The shape of the model 12 substantially corresponds with that of the prepared dental element, to which additional material corresponding to a cement layer to be inserted is added. In FIG. 3 the shape of the prepared dental element is indicated by a dashed line 13; the area beyond corresponds to the cement layer.

The dental crown 11 is manufactured by applying layer upon layer on the model 12 and, after applying a layer, subsequently grinding or cutting each layer down to the shape then desired on the basis of the computations of the CAD/CAM system. The various layers which have been successively applied can differ as regards nature or material. Thus a first layer may consist of a sintered metal, while subsequent layers may consist of various types of porcelain.

As FIG. 3 shows, the dental crown 11 has an edge 14. The inner surface 15 of the dental crown 11 is provided with an elevated part 16 spaced from the edge 14. Part 16 is located nearer the dashed line 13 than the part 17 of the inner surface which is located nearer the edge 14. The result of this is that the cement layer, which is provided between the dental crown 11 and the prepared dental element, will be thinner at the elevation 16 than near the edge 14 of the dental crown 11. At elevation 16 there may also be direct contact between the prosthesis 11 and the prepared dental element on which the prosthesis is fitted.

After forming the dental crown 11 according to FIG. 3 the model 12 is milled off or removed in another way, so that the dental crown may be fitted on the prepared dental element concerned.

Figure 4:
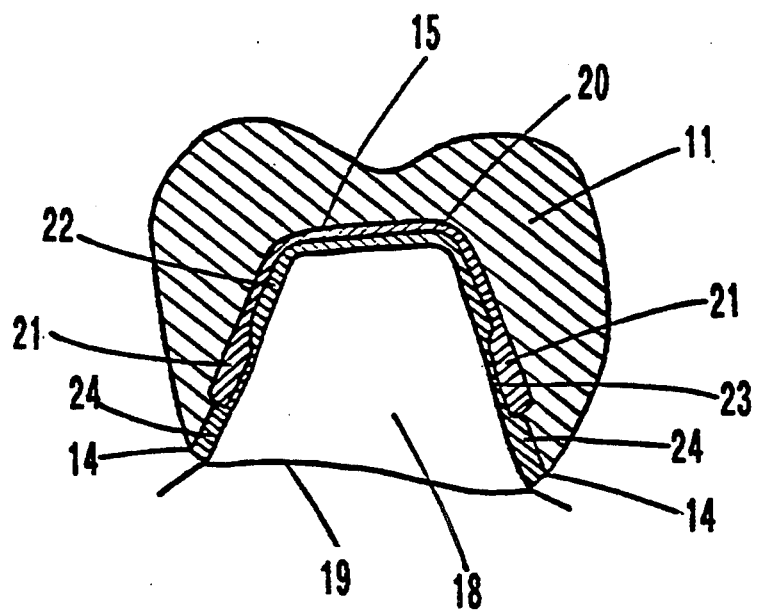
FIG. 4 shows a dental crown fitted on a prepared dental element.

FIG. 4 shows the dental crown 11, which is mounted on a prepared dental element 18, which is shown in elevational view. The dental element 18 has been suitably worked up to the preparation line 19. In FIG. 4 the dental crown is provided with a metal layer 20, which partially covers the inner surface 15 of the dental crown. The metal layer 20 serves to reinforce the dental crown, which is made of relatively brittle porcelain. The metal layer 20 does not extend up to the edge of the dental crown and has an thickened part 21, which constitutes the edge of the metal layer 20 in the shape of an annular strip. The thickness of the metal layer 20 is for example 0.1 mm.

A cement layer 22 is inserted between the dental crown 11 and the dental element 18, which cement layer fixes the dental crown 11 on the dental element 18. As appears from FIG. 4, the cement layer 22 does not comprise the same thickness all over. The cement layer 22 is thicker near the edge 14 than near the thickened part 21 of the metal layer 20. The thickness of the cement layer 22 may be reduced to such a degree, at that location, that in fact the dental crown 11 and the prepared dental element 18 are in direct contact.

Since the material of the cement layer 22 is slightly elastic and remains so, a local difference in the thickness of the cement layer 22 leads to a corresponding local difference in rigidity. The thinner part 23 of the cement layer 22 thus provides more support for the dental crown 11 than the thicker part 24 near the edge 14. As a result of that, forces, which are for example exerted on the dental crown during chewing, will be primarily transmitted to the dental element 18 via the thinner part 23 of the cement layer, so that the part of the dental crown near the edge 14, which is relatively thin and fragile, is protected from large forces being exerted thereon.

The invention is not restricted to the embodiment described. Many variations, for example as regards size and materials used, are possible when using the invention.

I claim:

1. A method for manufacturing a dental prosthesis, such as a dental crown, comprising the step of subjecting the outside visible part of the prosthesis to a material removing operation by means of a numerically controlled micro machine tool which follows machining paths along said prosthesis, wherein the machining paths follow three-dimensional irregularly spaced curved lines.

2. A method for manufacturing a dental prosthesis, such as a dental crown, comprising the step of subjecting the outside visible part of the prosthesis to a material removing operation by means of a numerically controlled micro machine tool which follows machining paths along said prosthesis, wherein the machining paths follow three-dimensional curved lines which are substantially circular paths around said prosthesis, with a varying local radius, and wherein the mutual distance between adjacent machining paths is larger at locations with a smaller radius than at locations where the paths have a larger radius.

3. A prosthesis formed by the method of claim 2.

4. A method according to claim 1 wherein machining lines are formed and are visible and on the prosthesis.

5. A method according to claims 1 or 4 wherein the shape of the outside of the prosthesis is numerically stored as a network of lines whose points of intersection are fixed and wherein the machining paths follow natural grooves of the surface of a model tooth, the mutual distance between machining paths substantially lies between 0.01 and 0.25 millimeters, and wherein said machining paths of the material removing operation follow said network lines.

6. A method according to claims 1 or 4 wherein a pointed burr follows fissures in the surface of the shape of a tooth used as a model for the shape of said prosthesis.

7. A prosthesis formed by the method of claim 4.

8. A method according to claim 1 wherein said three-dimensional curved lines follow natural lines of the surface of the shape of a tooth used as a model for the shape of said prosthesis.

9. A prosthesis formed by the method of claim 1.

* * * * *